(12) United States Patent
Kao et al.

(10) Patent No.: US 9,095,455 B2
(45) Date of Patent: Aug. 4, 2015

(54) BRAIN MACHINE INTERFACES INCORPORATING NEURAL POPULATION DYNAMICS

(71) Applicant: The Board of Trustees of the Leland Stanford Junior University, Palo Alto, CA (US)

(72) Inventors: Jonathan C. Kao, Stanford, CA (US); Paul Nuyujukian, Stanford, CA (US); Mark M. Churchland, New York, NY (US); John P. Cunningham, Saratoga, CA (US); Krishna V. Shenoy, Palo Alto, CA (US)

(73) Assignees: The Board of Trustees of the Leland Stanford Junior University, Palo Alto, CA (US); Cambridge Enterprise Limited, Cambridge (GB)

( * ) Notice: Subject to any disclaimer, the term of this patent is extended or adjusted under 35 U.S.C. 154(b) by 48 days.

(21) Appl. No.: 14/187,814

(22) Filed: Feb. 24, 2014

(65) Prior Publication Data

US 2014/0257520 A1  Sep. 11, 2014

Related U.S. Application Data

(60) Provisional application No. 61/773,976, filed on Mar. 7, 2013.

(51) Int. Cl.
*A61F 2/72* (2006.01)
*A61B 5/00* (2006.01)
*A61B 5/04* (2006.01)
*A61F 2/70* (2006.01)

(52) U.S. Cl.
CPC .............. *A61F 2/72* (2013.01); *A61B 5/04001* (2013.01); *A61B 5/7278* (2013.01); *A61F 2002/704* (2013.01); *A61H 2230/105* (2013.01)

(58) Field of Classification Search
None
See application file for complete search history.

(56) References Cited

U.S. PATENT DOCUMENTS 8,792,976 B2 *  7/2014  Gilja et al. .................... 600/545

FOREIGN PATENT DOCUMENTS

RU          2 415 642 C1 *  4/2011  .......... A61B 5/0476

OTHER PUBLICATIONS

Computer generated translation of the description and claims of RU 2 415 642 C1, published on Apr. 10, 2011.*
Churchland et al. (2012. Neural population dynamics during reaching. Nature 2012:487 (Jul. 5), 23 pages.

* cited by examiner

*Primary Examiner* — David H Willse
(74) *Attorney, Agent, or Firm* — Lumen Patent Firm

(57) ABSTRACT

A brain-machine interface is provided that incorporates a neural dynamical structure in the control of a prosthetic device to restore motor function and is able to significantly enhance the control performance compared to existing technologies. In one example, a neural dynamical state is inferred from neural observations, which are obtained from a neural implant. In another example, the neural dynamical state can be inferred from both the obtained neural observations and from the kinematics. A controller interfaced with the prosthetic device uses the inferred neural dynamical state as input to the controller to control kinematic variables of the prosthetic device.

10 Claims, 7 Drawing Sheets

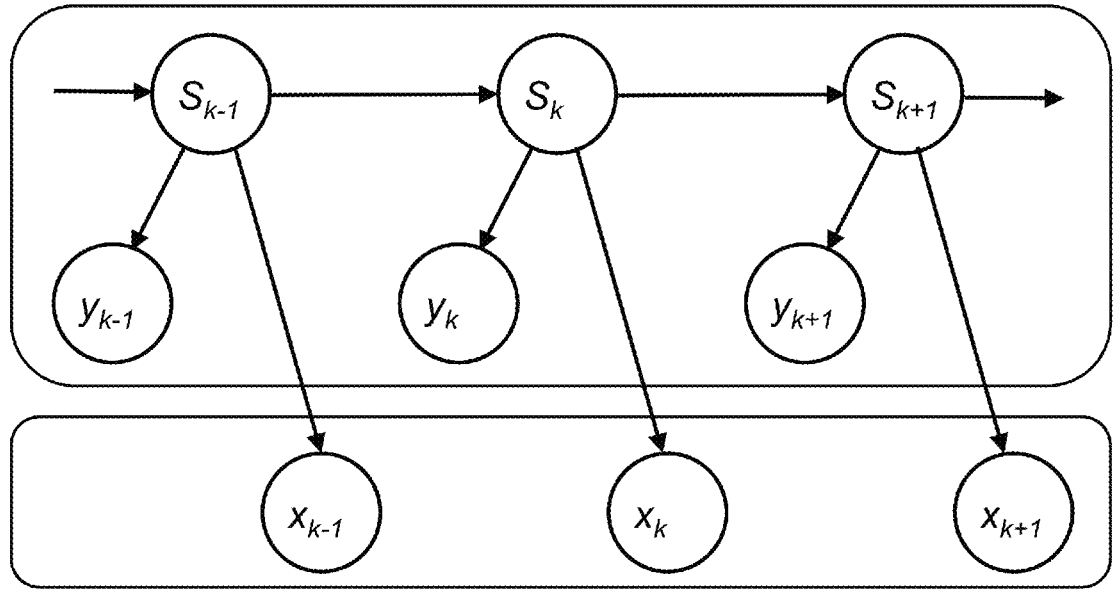
Fig. 2
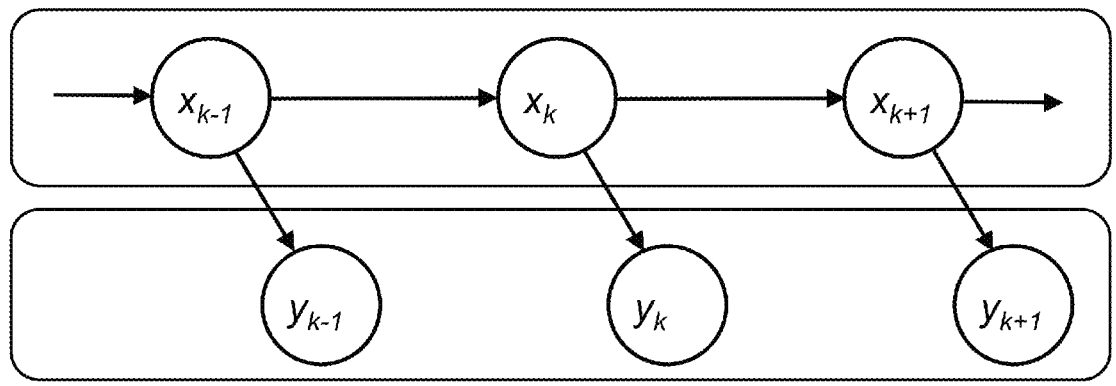
Fig. 3 (*prior art*)

BRAIN MACHINE INTERFACES INCORPORATING NEURAL POPULATION DYNAMICS

STATEMENT OF GOVERNMENT SPONSORED SUPPORT

This invention was made with Government support under grant no. DGE-1147470 awarded by the National Science Foundation, under grant no. R01-NS054283 awarded by the National Institutes of Neurological Disorders and Stroke, under grant no. HD075623 awarded by the National Institutes of Health, and under grant no. N66001-10-C-2010 awarded by the Defense Advanced Research Projects Agency (DARPA). The Government has certain rights in this invention.

FIELD OF THE INVENTION

This invention relates to methods, devices and systems for restoring lost motor function. In particular, the invention relates to brain-machine interfaces for controlling prosthetic devices.

BACKGROUND OF THE INVENTION

Millions of people are unable to move due to neurological injury or disease. Brain-machine interfaces (BMIs), which use neural signals to control prosthetic devices, seek to restore lost motor function to people suffering such neurological injury or disease (FIG. 1). Clinically relevant BMI systems including state-of-the-art Kalman filter techniques, population vector techniques, and BMIs used in clinical trials consider neural activity to be a noisy function of external kinematic parameters, such as arm velocity, but do not model the internal dynamics of the neural activity. Despite the great progress in this field, there is a strong need for enhancements of BMI performance to ensure clinical viability. It is therefore the objective of this invention is to provide a new class of brain-machine interface that incorporates neural dynamical structure, which is able to significantly enhance BMI performance over existing interfaces.

SUMMARY OF THE INVENTION

The present invention provides a brain-machine interface that incorporates a neural dynamical structure in the control of a prosthetic device to restore motor function. These new class of interfaces are able to significantly enhance control performance compared to existing technologies.

The brain-machine interface for restoring motor function obtains neural observations $y_k$ from a neural implant. Neural observations are defined by the spike frequency of a neuron (or multiple neurons simultaneously recorded on a single electrode) and are used to infer a neural dynamical state $s_k$ using a computer software program. The inferred neural dynamical state is a state of a dynamical system, which is defined by:

$$s_{k+1} = f(s_k) + g(u_k) + n_k$$

$$y_k = h(s_k) + l(u_k) + r_k$$

where $f(s_k)$ is a function describing how the neural dynamical state evolves over time from $s_k$ to $s_{k+1}$, where $h(s_k)$ is a function mapping the neural dynamical state $s_k$ to the neural observations $y_k$, where $(u_k)$ is an input to the dynamical system at time k, where $g(u_k)$ is a function mapping the input $u_k$ to the dynamical state $s_{k+1}$, where $l(u_k)$ is a function mapping the input $u_k$ to the neural observations $y_k$, where $n_k$ and $r_k$ are noise variables, and where k denotes time.

A controller interfaced with the prosthetic device uses the inferred neural dynamical state $(s_k)$ as input to the controller to control kinematic variables $(x_k)$ of the prosthetic device. The kinematic variables $(x_k)$ include position and velocity of the prosthetic device.

In one example, the state of the dynamical system is updated by a state update matrix M, and an observation mapping P, so that:

$$s_{k+1} = M s_k + n_k$$

$$y_k = P s_k + r_k$$

where $n_k$ has noise covariance N and $r_k$ has noise covariance R.

In another example, the neural dynamical state can be inferred from both the obtained neural observations $(y_k)$ and from the kinematics $(x_k)$, according to:

$$s_{k+1} = f(s_k) + g(u_k) + n_k$$

$$a(y_k, x_k) = h(s_k) + l(u_k) + r_k$$

where $a(y_k, x_k)$ is a function of the kinematics $x_k$ and the neural observations $y_k$. Here, the inferred neural dynamical state $(s_k)$ and the neural observations $(y_k)$ are then input to the controller to control the kinematic variables $(x_k)$ of the prosthetic device.

BRIEF DESCRIPTION OF THE DRAWINGS

FIG. 2 shows according to an exemplary embodiment of the invention a graphical representation of a neural dynamical filter or a computer-implemented inference system, modeling the dynamics of the neural state $(s_k)$. The neural state propagates from time k to time k+1 obeying modeled neural population dynamics, at each point in time generating both the kinematics $(x_k)$ and the observed neural data $(y_k)$.

FIG. 3 shows according to a prior art example a graphical representation of the linear dynamical system underlying kinematic-state Kalman filters, where the kinematics $(x_k)$ are related through a linear dynamical update rule, and are causal to neural observations $(y_k)$. It is noted that there is no temporal structure modeled in the neural activity.

In FIG. 6A, we allow the kinematics ($x_k$) to have a dynamical update law, so that they are smooth over time. In FIG. 6B, we model both the kinematics and the neural state as part of a dynamical system that is generative of neural data ($y_k$). In FIG. 6C, we allow the kinematics to be inferred through a cascade of Kalman filters, where there is first a neural dynamical system to infer the neural state ($s_k$) from the neural data ($y_k$), and the second is a kinematic dynamical system to infer the kinematics ($x_k$) from the neural state.

DETAILED DESCRIPTION

Figure 1:
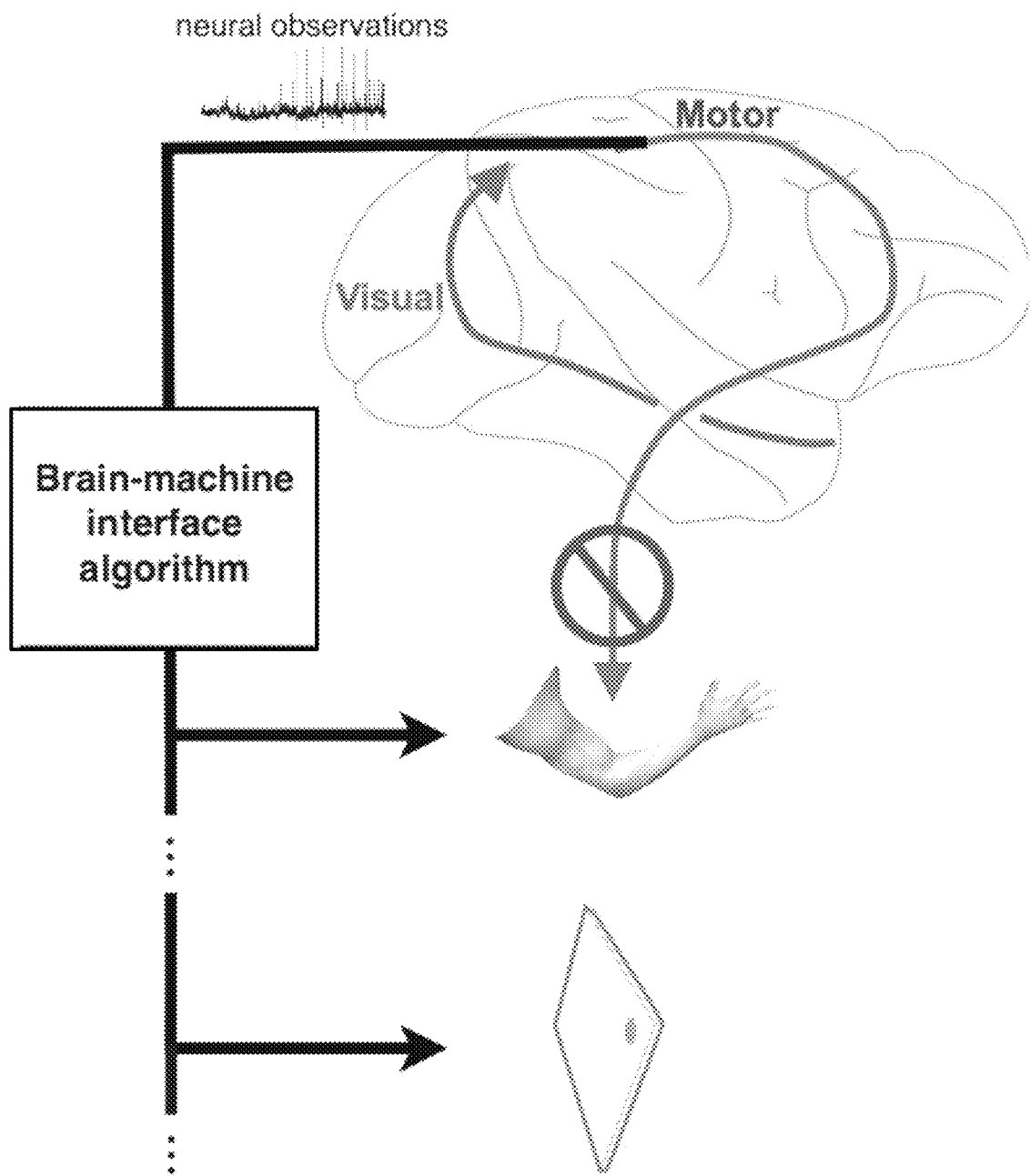
FIG. 1 shows according to the invention a brain-machine interface, which uses neural signals to control a prosthetic device with the aim to restore lost motor function to people suffering such neurological injury or disease.

The basis for this invention is the realization that neural population activity is not exclusively a function of external kinematic drive. Instead, it may have its own internal drive, with rules that govern how the neural population responses modulate themselves over time. By learning these rules, or neural dynamics, past neural population activity can be informative of newly observed and noisy neural activity.

As Brain Machine Interfaces (BMIs) universally encounter neural responses that are noisy and potentially far more complex than the kinematics used to describe them, a framework to incorporate neural dynamical information may enable substantial performance improvements across BMI systems. The present invention provides a different framework for BMI control algorithm design, which for the first time incorporates a neural dynamical model and captures both internally and externally driven activity.

In closed-loop experiments, we have demonstrated that incorporating neural population dynamics in a BMI system can significantly increase the performance throughput (or achieved bitrate) by 83% and 31% in two rhesus macaques. These advances, which can be algorithmically incorporated into most BMI systems, demonstrate that we can infer rich and coherent dynamical structure in motor cortical neural responses that can be used to substantially increase the performance of BMI systems.

To incorporate the neural dynamics of motor cortex into a BMI system, we designed the BMI based on a dynamical systems framework of motor control. In this framework, the observed neural population spike counts at time k, $y_k$, can be interpreted as a noisy observation reflecting a low-dimensional (low being relative to the dimensionality of $y_k$) and dynamical neural state signal, $s_k$, which summarizes and captures the essential dimensions of motor cortical activity. In one example, we modeled this dynamical system in the linear Gaussian form as:

$$s_{k+1} = Ms_k + n_k \quad (1)$$

$$y_k = Ps_k + r_k \quad (2)$$

where $n_k$ and $r_k$ are Gaussian noise terms. Matrix M, which we learned exclusively from the neural observations, models the internal drive of the neural population activity (Supplementary Methods 2.1). A BMI system which then decodes the prosthesis kinematics, $x_k$, from the neural state, $s_k$ (as opposed to the noisy neural observations, $y_k$), incorporates a model of the temporal structure of the neural population activity, whereby $s_k$ is informative of $s_{k+1}$.

An example of such a system is graphically represented in FIG. 2. This approach is in contrast to state-of-the-art techniques in BMI decoders (FIG. 3), including kinematic-state Kalman filtering (KKF) techniques, which do not capture or infer temporal structure in the neural activity. Instead, these techniques model a generative process where the neural population activity is a function of kinematic variables that are smooth over time. While external or intended kinematic variables, as well as the physical laws they obey may be represented in motor cortex, there is evidence that the dynamics of motor cortical population activity is richer than those described by kinematic representations.

Modeling these neural dynamics, which capture complexities in the neural responses, which cannot be explained by kinematics alone, may help to address an important challenge faced by all BMI systems: decodes occur on single trials, where neural observations are notoriously noisy.

Figure 4:
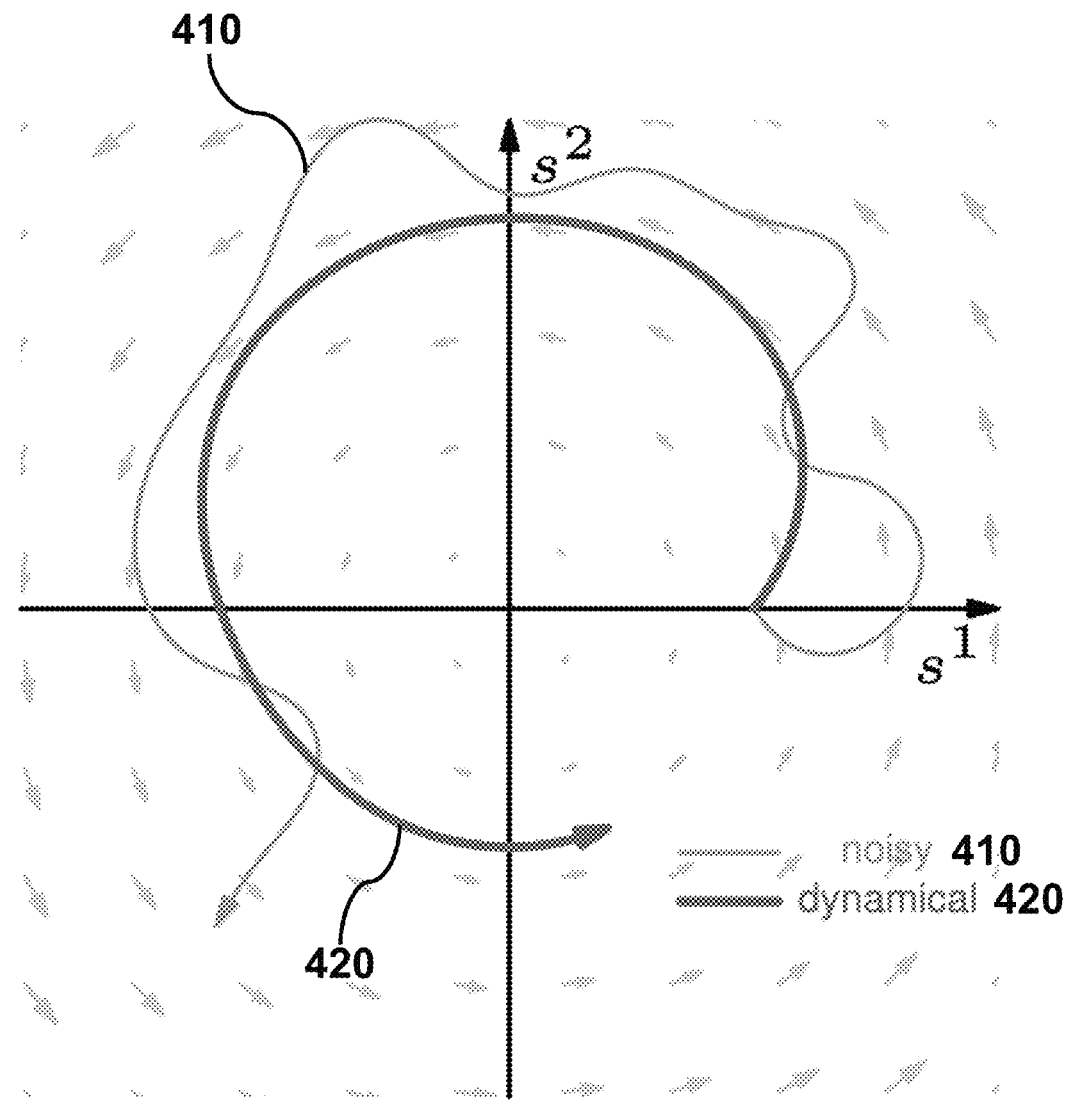
FIG. 4 shows according to an exemplary embodiment of the invention a two-dimensional (2D) projection in neural state space. The arrows indicate the dynamics of the neural state, so that for the purposes of this example, it tends to rotate counterclockwise. When the dynamics are not taken into account, the observed single trial neural state trajectory can be noisy ('noisy' trace 410) because neural activity is noisy on single trials. However, if the dynamics of the neural population are known, the single trial trajectory noise may be ameliorated by taking neural dynamical information into account ('dynamical' trace 420).

Consider a flow field shown in FIG. 4 in which the dynamics 410 of the neural state obey purely rotational dynamics. A neural state trajectory inferred from the observed population activity alone, without modeling the population dynamics, will be very noisy, as shown by trajectory 420 in FIG. 4. If, in addition to neural observations, we had knowledge that the neural trajectories obeyed dynamics as indicated by the flow field, this information could be used to augment our estimate of the noisy single trial neural state trajectory, as shown by 420 in FIG. 4. If the modeled dynamics accurately describe how the neural population activity evolves over time, the neural state trajectory may be a de-noised decode control signal for BMI systems.

To demonstrate this, we first trained two rhesus macaques (monkeys J & L) to acquire targets positioned on a grid with a virtual computer cursor. Monkeys J & L were implanted with 192 and 96 electrodes (Utah electrode array) respectively in the dorsal premotor and primary motor regions of cortex (Methods). These regions have been found to exhibit population-level dynamics that can be approximately captured using a linear model. The performance of Monkeys J & L was evaluated by quantifying the achieved communication bitrate on the grid task, which is a measure of the achieved information (bits) conveyed by the number of net correct selections, divided by the time spent to make all selections. This measure is not a theoretical limit, nor relies on any coding schemes, and as such is a true achieved level of performance (Supplementary Methods 1.2).

We performed three comparisons to determine (1) if incorporating neural dynamics could improve the performance a BMI algorithm over the same algorithm that did not incorporate neural dynamics, (2) if a BMI capturing motor cortical neural dynamics could outperform a BMI that captures only kinematic dynamical laws, and (3) if a BMI using only a linear approximation of the neural dynamics could outperform the most general linear BMI.

We built the model of FIG. 2 as a computer-implemented model by learning an autonomous latent-state dynamical system, as described by Equations 1-2. We specified the dimensionality of the latent neural state to be 20, so that it is of sufficiently high dimensionality to capture a significant proportion of neural signal variance. We put no constraint on the characteristics of the learned dynamics. After learning the parameters of the dynamical system via expectation maximization (Supplementary Methods 2.1), the neural state was inferred online by using a Kalman filter, so that the estimated neural state $\hat{s}_k$ was a linear combination of the dynamical evolution of the previous neural state estimate, $\hat{s}_{k-1}$, and the newly observed spike counts, $y_k$.

For the first comparison, we evaluated the performance of a decoder where the kinematics were decoded by a least-squares regression to the dynamical neural state versus the non-dynamical observed spike counts. Thus, we found ($L_s$, $b_s$) and ($L_y$, $b_y$) via least squares, such that:

$$\hat{x}_k = L_s \hat{s}_k + b_s \quad (3)$$

$$\hat{x}_k = L_y y_k + b_y \quad (4)$$

We refer to Equation 3 as the neural dynamical filter (NDF), while Equation 4 is the optimal linear estimator (OLE). To ensure the benefit of dynamics was not solely due to a smoothness provided by neural linear dynamics, we smoothed the neural spike counts, $y_k$, by convolution with causal Gaussian kernels having standard deviations ranging from 25 to 200 ms. We used a least-squares regression (1) so that more complex modeling, such as noise modeling, would not obfuscate results and (2) to design a model where neural activity is causal to external kinematics, as is consistent with physiology. Over 13 experimental sessions, we evaluated the performance of the NDF and OLE algorithm in closed-loop BMI control. We have demonstrated that a BMI incorporating neural dynamics achieves significantly higher performance (as measured by information throughput) than its non-dynamical counterpart.

The NDF achieved 31% and 83% higher performance than the best OLE decoder in Monkeys J & L, respectively (p<0.01, paired t-test). We also found that the NDF achieved higher success rates than the OLE, which demonstrates that incorporating neural dynamical modeling into a BMI algorithm can substantially increase its performance.

For the second comparison, we evaluated the performance of the NDF versus the KKF. While the KKF incorporates a dynamical model over the relatively low-dimensional kinematic variables, the NDF incorporates dynamics derived from the neural population activity that are higher-dimensional and richer. Thus, we evaluated (1) whether it is better to use a dynamical model of a latent neural space, as opposed to those of the kinematic variables, and (2) if smoothing via Kalman filtering, which incorporates the noise properties of a dynamical system, is the principal reason for the increased performance observed in the NDF. Over 6 experimental sessions, we found that the NDF performed significantly better than the KKF (47% and 61% improvement in Monkeys J and L, respectively, p<0.01, paired t-test) and that the NDF achieved significantly higher success rates and quicker acquire times than the KKF.

Thus, a decoder incorporating the dynamics of the neural population achieves higher performance than one that only models a dynamical update law for the kinematics. This suggests that our model of the neural dynamics is capturing meaningful structure in the neural population activity that is not described by kinematic dynamical representations alone. For example, modeling the dynamics of the neural population activity results in decoders where the direction in which a particular channel can drive the decoder (the 'preferred direction') is not necessarily static, in contrast to the OLE and KKF decoders.

In the third comparison, we evaluated the performance of the NDF versus the Wiener filter (WF). The WF finds the optimal linear least-squares coefficients, $L_0, L_1, \ldots, L_{p-1}$, to decode the current kinematics as a function of a history of neural data, so that:

$$\hat{x}_k = \Sigma_{j=0}^{p-1} L_j y_{k-j}. \quad (5)$$

Any linear state-estimation in a dynamical system can be written as a linear operation on a history of the observed data. In this sense, the WF represents the most general model of any linear approach: the OLE, KKF, and NDF can be written in the form of Equation 5. We observed that the WF achieved higher bitrates in closed-loop control than the OLE and KKF, in contrast to previously reported experimental results, potentially because we optimized the parameters of the WF (including the amount of history used, as well as the amount of regularization) in closed-loop experiments. However, we found that the NDF performed significantly better than the WF (16% and 13% improvement in Monkeys J and L, respectively, p<0.01, paired t-test), acquiring targets at higher success rates. Thus, even with the limitation that the modeled neural dynamics are linear, which may be an oversimplified assumption, we found that directly modeling the neural dynamics resulted in performance that could not be matched by brute force linear regression. Hence, modeling neural dynamics captures coherent properties of the neural population that are not extracted by least-squares regression over a history of neural data, even though this approach could in principle capture neural dynamics. This suggests that the neural dynamics are an emergent property of the motor cortical neural responses, and that incorporating these dynamics may be a crucial component in enabling higher-performance, next-generation, BMI systems.

We analyzed the modeled neural dynamics matrices, M, to characterize and visualize the learned neural state dynamics. Because the dynamics were learned in an unsupervised fashion, the matrix M converged almost surely to a non-normal matrix with complex eigenvalues. We found that many of the eigenvalues of $\tilde{M}$, the first-order continuous Euler approximation of M, had time constants of decay on the order of hundreds of milliseconds, with frequencies ranging as high as 2.5 Hz.

We also visualized the vector flow fields in sub-planes according to the dynamics of the chosen dimensions. In most 3-dimensional spaces, we found that the dynamics were contractive and rotational, while it was also possible to find planes that demonstrated little contraction. We note that this view of the dynamics is incomplete since the modeled dynamics are 20-dimensional, so that other dimensions of the neural state (not shown) are coupled to the plotted dimensions. Nevertheless, we show the evolution of the estimated neural state for various reach conditions, which cluster in the neural state space based on the reach condition.

Figure 5:
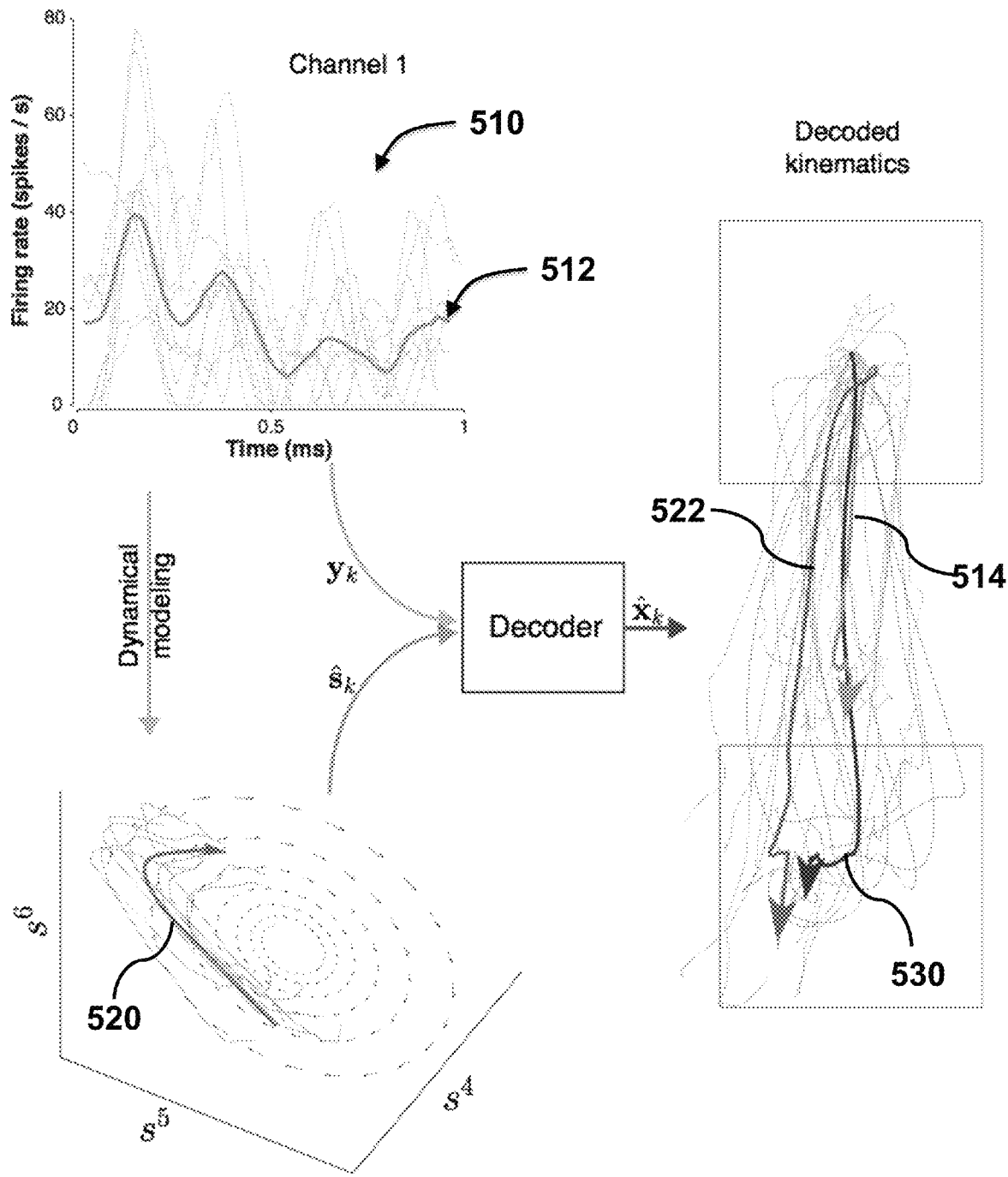
FIG. 5 shows according to an exemplary embodiment of the invention the inference or decoding with a dynamical neural state as opposed to noisy neural observations. An inference or decode algorithm accepts neurally-derived observations and outputs decoded kinematics, $\hat{x}_k$. Most BMI systems decode from noisy neural observations, $y_k$, which comprise the single trial spike counts of the neural data. This data (smoothed) is shown for a single channel, where traces 510 denote the single trial neural observations when a monkey intended to reach downwards. The bold trace 512 is the firing rate averaged over trials, or peri-stimulus time histogram, and is sufficiently complex that its multiphasic response may not be well-described by typically monophasic kinematic variables, such as, cursor velocity in a pointing task. In our framework, instead of using the neural data, $y_k$ to drive the decoder, we instead first perform neural dynamical modeling to derive an estimated neural state trajectory, $\hat{s}_k$. Here, we show 3 dimensions of a 20-dimensional neural trajectory in a subspace where the modeled dynamics were found to be largely rotational. Note that because the neural state is 20 dimensional, a 3-dimensional view is incomplete, since the other dimensions of the neural state also affect the neural trajectory in the depicted dimensions (dimensions 4-6). For this specific example, we found that for the condition where a monkey intends to reach downwards, the single-trial neural trajectories roughly followed the dynamics of the subspace. This estimated and de-noised neural state, $\hat{s}_k$, is then used to drive the inference model/decoder. We show offline kinematic reconstructions ($\hat{x}_k$) when the same algorithm is driven by the neural observations, $y_k$ (512), versus the neural state, $s_k$ (520). Trace 530 denotes the average true path of the cursor for the given trial when the monkey reaches from the upper box to the lower box. The offline reconstructions using the dynamical neural state result in a superior offline decode when compared to using the non-dynamical binned spike counts. In this figure, both the neural state and the corresponding decoded trajectory are 522, and both the single trial firing rates and the corresponding decoded trajectory are 514.

By modeling a linear time-invariant approximation to the neural dynamics governing a reaching task, we observed a significant increase in the performance of a BMI algorithm. Importantly, this advance is not a stand-alone algorithm, but rather represents a critical component in BMI design that can be combined with a diverse class of BMI algorithms and innovations, such as the intention estimation innovations of the ReFIT-KF algorithm, closed-loop decoder adaptation approaches, and even nonlinear approaches, as schematically shown in FIG. 5. As computational motor neurophysiology continues to improve our understanding and modeling of the dynamics underlying motor cortical regions, the performance of neural dynamically-based BMI algorithms may continue to increase. These results demonstrate that there are coherent motor cortical neural dynamics that can be learned and used to significantly increase BMI performance, which may be critical for enabling higher-performance BMI systems.

Methods

Experiments were conducted with adult male rhesus macaques (J & L) implanted with 96 electrode Utah arrays (Blackrock Microsystems Inc., Salt Lake City, Utah) using standard neurosurgical techniques. Electrode arrays were implanted in dorsal premotor cortex (PMd) and primary motor cortex (M1) as visually estimated from local anatomical landmarks. Monkey J had two arrays, one in M1 and one in PMd, while Monkey L had one array implanted on the M1/PMd border. The monkeys made point-to-point reaches in a 2D plane with a virtual cursor controlled by the contralateral arm or by a BMI. The virtual cursor and targets were presented in a 3D environment. Hand position data were measured with an infrared reflective bead tracking system (Polaris, Northern Digital, Ontario, Canada). Spike counts were collected by applying a single negative threshold, set to 4.5×root-mean-square of the spike voltage per neural channel. For neural observations used for the decoders, binned threshold crossings were counted in non-overlapping 15 ms bins. Behavioral control and neural decode were run on separate PCs using Simulink/xPC platform (Mathworks, Natick, Mass.) with communication latencies of 3 ms. This enabled millisecond timing precision for all computations. Neural data were initially processed by the Cerebus recording system (Blackrock Microsystems Inc., Salt Lake City, Utah) and were available to the behavioral control system within 5 ms±1 ms. Visual presentation was provided via two LCD monitors with refresh rates at 120 Hz, yielding frame updates of 7 ms±4 ms. Two mirrors visually fused the displays into a single three-dimensional percept for the user, creating a Wheatstone stereograph. We selected our animal model based on what we believe most closely mimics the neural state of a human subject that would be employing a BMI in a clinical setting.

Supplementary Methods 1. Tasks

For all experiments conducted in this work, two tasks were utilized. The first was a center-out-and-back reaching task, which was used as a training set for each decoder. The second was a grid task, which was used to evaluate the performance of each decoder. The grid task was used as the evaluation task because it is a selection task that can convey information in a clinically relevant way. Therefore the grid task allows the computation of an achieved bitrate, which quantifies the rate at which the BMI can communicate information.

1.1 Center-Out-and-Back Task

In the center-out-and-back task, eight targets were placed with uniform spacing on the circumference of a 12 cm radius circle. The subject was required to acquire the center target, followed by one of the eight (randomly chosen) radial targets. The subject was given 2 seconds to acquire each prompted target. After successful acquisition of a radial target, or following the failure to acquire any target, the subject was prompted to acquire the center target. Each target had a 4 cm by 4 cm acceptance window centered around the target. For every target selection, the subject had to hold the cursor within the acceptance window of the target for 500 contiguous milliseconds. Training sets were comprised of 500 successful trials during which the subject would repeatedly acquire peripheral and central targets.

1.2 Grid Task

The grid task utilized a 6 by 6 array of targets, each with a 4 cm by 4 cm acceptance window. The targets were tiled end-to-end contiguously to create a workspace that was 24 cm by 24 cm. This grid of targets mimics a keyboard task where the subject can select any of 36 targets at any time by dwelling in the acceptance window of a target for 450 ms. Because any target can be selected at any time, a correct target selection conveys information; for example, the targets could be alphanumeric characters or symbols from a keyboard. To evaluate performance, the subject had to acquire one prompted target out of the potential 36 targets. Although only one target was prompted, every target was selectable by dwelling on it for 450 ms. The subject was given 5 seconds to acquire the prompted target; if no target was selected in 5 seconds, no target selection would be made. Following target selection, a lock-out time of 200 ms was enforced, during which dwell time was not counted; this was done to account for the reaction time of the subject. Targets were randomly chosen according to a uniform distribution, and therefore, the information conveyed per target selection is $\log_2(36)$ bits. To be conservative in the estimation of achieved bitrate, we compensated every incorrect selection with a correct selection, much like an incorrect selection on a keyboard must be corrected by pressing the delete key. Therefore, the information conveyed on the grid task is calculated by considering the net number of correctly selected targets. Hence, performing the task at a success rate of 50% results in a bitrate of 0 bps, so that no information is conveyed through the task. We calculated an achieved information rate (bitrate) by dividing the amount of information conveyed during target acquisition by the time taken to acquire the targets. Therefore, if in T seconds, c correct selections were made, while l incorrect selections were made, the bitrate was calculated to be:

$$I = \frac{(c-l)\log_2(36)}{T}, \text{ if } l > c$$

and I=0 if c<l. This is the achieved bitrate of the decoder on the grid task. To evaluate the performance of a decoder, the monkey performed the grid task in blocks of approximately 100 trials, from which the bitrate was calculated.

2. Decode Algorithms

The decoded kinematics are the 2D position ($\hat{p}_k$) and 2D velocity ($\hat{v}_k$) of a computer cursor. Neural spikes were counted in non-overlapping 15 ms bins, and were used as the observations for all decode algorithms. Our choice of bin width is informed by a previous result for online BMI systems, which demonstrated that smaller bin widths lead to increased performance. Given that the decoded position and velocity of the cursor at time k were $\hat{p}_k$ and $\hat{v}_k$ respectively, the decoded position shown to the subject, $p_k$, was calculated as:

$$p_k=(1-\alpha)\hat{p}_k+\alpha(p_{k-1}+v_{k-1}\Delta t)$$

with $\alpha=0.975$ and $\Delta t$ being the bin width of the decoder. This indicates that the final decoded position is a weighted sum, with 2.5% contribution from the decoded position, and 97.5% contribution from the integrated velocity. The small position contribution in part stabilizes the position of the decoder in the workspace. The importance of taking into account the position contribution of the signal has been noted.

Decoders were trained using data collected while a subject made reaches on a center-out-and-back task for 500 successful trials. Although the decoders were trained using data collected while the subject performed a center-out-and-back task, all decoders were evaluated on the grid task.

2.1 Neural Dynamical Filter

To learn a neural dynamical filter (NDF), we modeled the following latent state linear dynamical system:

$$s_{k+1}=Ms_k+n_k$$

$$y_k=Ps_k+r_k$$

where $n_k$ and $r_k$ are zero mean Gaussian noise terms with diagonal covariance matrices N and R, respectively. We learned this latent state linear dynamical system in an unsupervised fashion from the sequence of observed neural activity. The time-series of neural observations $\{y_k\}_{k=1,\ldots,K}$ treated as the observed output of a latent state linear dynamical system (LDS). We did not perform any pre-processing steps on the binned spike counts, $y_k$. Expectation maximization (EM) was performed to learn the parameters M, P, N, R. When performing EM, we utilized an approximation in the E-step: we assumed that the Kalman smoothing parameters remained constant after convergence of the estimated state covariance matrix within reasonable tolerance. Due to the possibility of finding local maxima with the EM algorithm, we initialized the EM algorithm on each experimental day using previously learned dynamical systems, as well as from a factor analysis initialization. Initialization from a previously learned LDS also decreased the convergence time. We briefly evaluated the performance of NDF algorithms using each of the learned dynamical systems, and chose the one with the highest performance.

After learning the parameters of the latent state dynamical system via EM, we used the steady-state form of the Kalman filter to estimate the neural state, $\hat{s}_k$, at each point in time from the sequence of neural observations, $y_k$, in the training data. It was reasonable to use the computationally efficient steady-state form of the Kalman filter, since convergence occurred on the order of seconds. From the sequence of decoded neural states, $\hat{S}=[\hat{s}_1 \hat{s}_2 \ldots \hat{s}_K]$ and the sequence of observed training set kinematics, $X=[x_1 x_2 \ldots x_K]$, we then found the matrix L which minimizes the mean squared error, $\|X-L_s[\hat{S}1]\|$, where the 1 term accounts for the bias. The solution is $L_s=X\hat{S}^T(\hat{S}\hat{S}^T)^{-1}$.

Variations

Figure 6A:
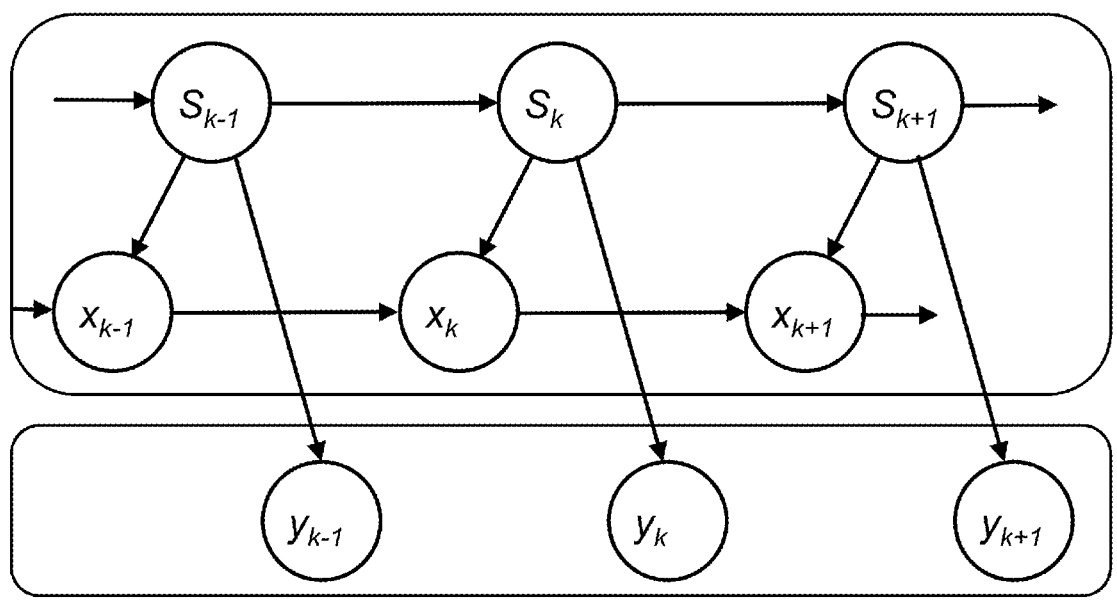
FIGS. 6A-C show according to exemplary embodiments of the invention graphical representations of variations of a neural dynamical filter/inference model/decoder with reference to FIG. 2, modeling the dynamics of the neural state ($s_k$). In every model, the neural state propagates through time obeying modeled neural dynamics. However, in these exemplary models we incorporate other and different assumptions.
Figure 6B:
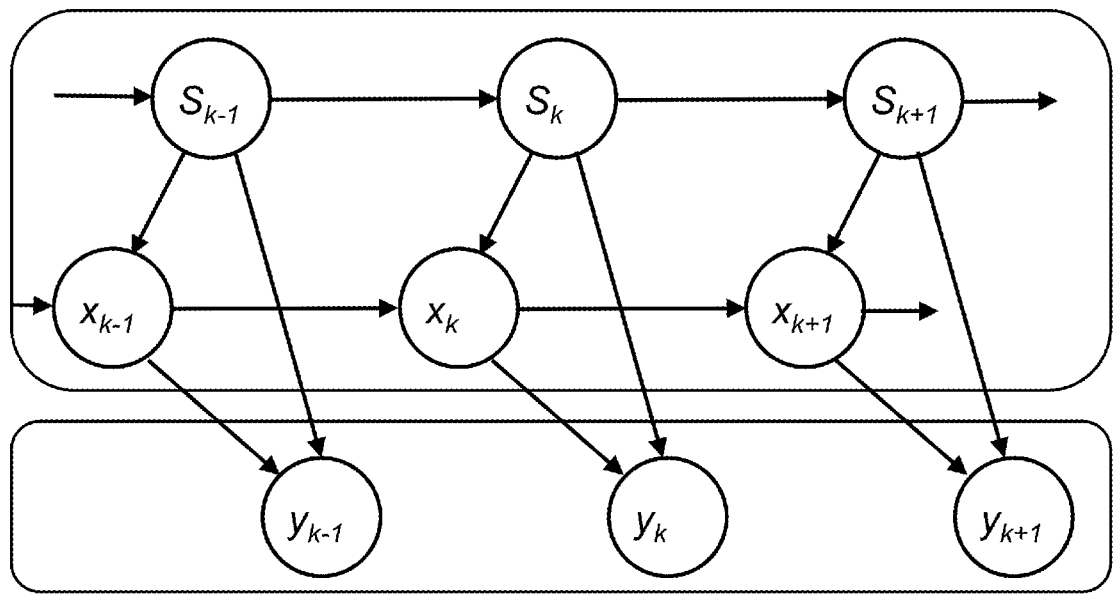
Figure 6C:
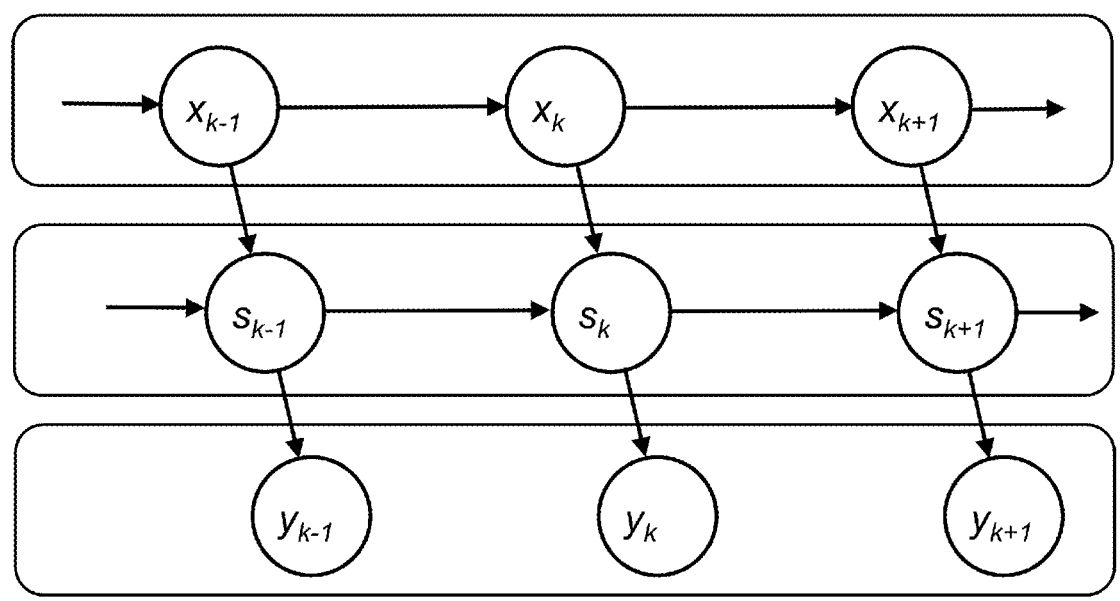

The BMI architecture shown in FIG. 2 could be varied within the scope of the invention, which is the incorporation of neural dynamics in a BMI. FIG. 6A-C shows exemplary architectures. It is noted that other architectures not shown are also within the scope of the invention as any architecture involving a latent neural state ($s_k$) and its dynamics (links between the $s_k$) fall into this class of decoders. Variations could include varying the graphical model(s) to incorporate kinematic dynamics, as shown in FIGS. 6A-C, varying the dimensionality of the underlying neural state, varying the technique to learn the dynamics of the underlying neural state, varying the actual dynamics of that the neural state obeys (linear, nonlinear, skew-symmetric, etc.), using multiple dynamical systems models that are switched based off of an HMM, or variant of an HMM, using dynamics to recover performance under neuron loss, by remembering the kinds of dynamics present when more neurons could be observed, or the like.

The inference model, decoder and/or controller can be computer-implemented as software and executed by a computer device, coded on a computer chip or chip implant. The inference model, decoder and/or controller can be on the same device, chip or implant or each have their individual software/hardware implementation.

What is claimed is:

1. A brain-machine interface for restoring motor function, comprising:
    (a) a neural implant for obtaining neural observations $y_k$, wherein the neural observations are defined by a spike frequency of one or more neurons;
    (b) a computer-implemented inference system for inferring a neural dynamical state $s_k$ from the obtained neural observations ($y_k$), wherein the inferred neural dynamical state is a state of a dynamical system which is defined by:

$$s_{k+1}=f(s_k)+g(u_k)+n_k$$

$$y_k=h(s_k)+l(u_k)+r_k$$

where $f(s_k)$ is a function describing how the neural dynamical state evolves over time from $s_k$ to $s_{k+1}$,
    where $h(s_k)$ is a function mapping the neural dynamical state $s_k$ to the neural observations $y_k$,
    where ($u_k$) is an input to the dynamical system at time k,
    where $g(u_k)$ is a function mapping the input $u_k$ to the dynamical state $S_{k+1}$,
    where $l(u_k)$ is a function mapping the input $u_k$ to the neural observations $y_k$,
    where $n_k$ and $r_k$ are noise variables, and
    where k denotes time;
    (c) a prosthetic device; and
    (d) a controller interfaced with the prosthetic device, wherein the inferred neural dynamical state ($s_k$) is input to the controller to control kinematic variables ($x_k$) of the prosthetic device.

2. The brain-machine interface as set forth in claim 1, wherein the kinematic variables ($x_k$) include position and velocity of the prosthetic device.

3. The brain-machine interface as set forth in claim 1, wherein the state of the dynamical system is updated by a state update matrix M, and an observation mapping P, so that:

$$s_{k+1}=Ms_k+n_k$$

$$y_k=Ps_k+r_k$$

where $n_k$ has noise covariance N and $r_k$ has noise covariance R.

4. The brain-machine interface as set forth in claim 1, wherein the neural dynamical state is inferred from the obtained neural observations ($y_k$) and from the kinematics ($x_k$) according to:

$$s_{k+1}=f(s_k)+g(u_k)+n_k$$

$$a(y_k,x_k)=h(s_k)+l(u_k)+r_k$$

where $a(y_k, x_k)$ is a function of the kinematics $x_k$ and the neural observations $y_k$.

5. The brain-machine interface as set forth in claim 1, wherein the inferred neural dynamical state ($s_k$) and the neural observations ($y_k$) are input to the controller to control the kinematic variables ($x_k$) of the prosthetic device.

6. A method of controlling a prosthetic device for restoring motor function, comprising:
(a) obtaining neural observations $y_k$, wherein the neural observations are defined by a spike frequency of one or more neurons;
(b) inferring through a computer-implemented method a neural dynamical state $s_k$ from the obtained neural observations $y_k$, wherein the inferred neural dynamical state is a state of a dynamical system which is defined by:

$$s_{k+1}=f(s_k)+g(u_k)+n_k$$

$$y_k=h(s_k)+l(u_k)+r_k$$

where $f(s_k)$ is a function mapping how the neural dynamical state evolves over time from $s_k$ to $s_{k+1}$,
where $h(s_k)$ is a function mapping the neural dynamical state $s_k$ to the neural observations $y_k$,
where ($u_k$) is an input to the dynamical system at time k,
where $g(u_k)$ is a function mapping the input $u_k$ to the dynamical state $s_{k+1}$,
where $l(u_k)$ is a function mapping the input $u_k$ to the neural observations $y_k$,
where $n_k$ and $r_k$ are noise variables, and
where k denotes time; and
(c) controlling the prosthetic device, wherein the inferred neural dynamical state ($s_k$) is input to the controller to control kinematic variables ($x_k$) of the prosthetic device.

7. The method as set forth in claim 6, wherein the kinematic variables ($x_k$) include position and velocity of the prosthetic device.

8. The method as set forth in claim 6, wherein the state of the dynamical system is updated by a state update matrix M, and an observation mapping P, so that:

$$s_{k+1}=Ms_k+n_k$$

$$y_k=Ps_k+r_k$$

where $n_k$ has noise covariance N and $r_k$ has noise covariance R.

9. The method as set forth in claim 6, wherein the inferring comprises inferring the neural dynamical state ($s_k$) from the obtained neural observations $y_k$ and from the kinematics $x_k$ according to:

$$s_{k+1}=f(s_k)+g(u_k)+n_k$$

$$a(y_k,x_k)=h(s_k)+l(u_k)+r_k$$

where $a(y_k, x_k)$ is a function of the kinematics $x_k$ and the neural observations $y_k$.

10. The method as set forth in claim 6, wherein the inferred neural dynamical state ($s_k$) and the neural observations ($y_k$) are input to the controller to control the kinematic variables ($x_k$) of the prosthetic device.

* * * * *